(12) United States Patent
Schilling et al.

(10) Patent No.: US 12,048,757 B2
(45) Date of Patent: *Jul. 30, 2024

(54) EMBOSSED EFFECT PIGMENT AND METHOD OF MANUFACTURE OF EMBOSSED EFFECT PIGMENT

(71) Applicant: ECKART GmbH, Hartenstein (DE)

(72) Inventors: Christine Schilling, Hartenstein (DE); Ann-Katrin Gebhard, Hartenstein (DE); Ulrich Schmidt, Hartenstein (DE); Oliver Struck, Hartenstein (DE)

(73) Assignee: Eckart GmbH, Hartenstein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,079

(22) Filed: Feb. 15, 2023

(65) Prior Publication Data

US 2023/0190597 A1 Jun. 22, 2023

Related U.S. Application Data

(63) Continuation of application No. 16/756,161, filed as application No. PCT/EP2018/078505 on Oct. 18, 2018, now Pat. No. 11,617,707.

(30) Foreign Application Priority Data

Oct. 18, 2017 (EP) .................................. 17001718

(51) Int. Cl.
| | |
|---|---|
| *A61K 8/26* | (2006.01) |
| *A61K 8/02* | (2006.01) |
| *A61K 8/19* | (2006.01) |
| *A61K 8/34* | (2006.01) |
| *A61K 8/36* | (2006.01) |
| *A61K 8/55* | (2006.01) |
| *A61K 8/58* | (2006.01) |
| *A61K 8/81* | (2006.01) |
| *A61Q 3/02* | (2006.01) |
| *C09C 1/00* | (2006.01) |
| *C09C 1/64* | (2006.01) |

(52) U.S. Cl.
CPC .............. *A61K 8/26* (2013.01); *A61K 8/0254* (2013.01); *A61K 8/19* (2013.01); *A61K 8/34* (2013.01); *A61K 8/361* (2013.01); *A61K 8/55* (2013.01); *A61K 8/585* (2013.01); *A61K 8/8117* (2013.01); *A61K 8/8176* (2013.01); *A61Q 3/02* (2013.01); *A61K 2800/412* (2013.01); *A61K 2800/437* (2013.01); *A61K 2800/612* (2013.01); *C01P 2004/51* (2013.01); *C01P 2004/61* (2013.01); *C01P 2006/65* (2013.01); *C09C 1/0051* (2013.01); *C09C 1/006* (2013.01); *C09C 1/0066* (2013.01); *C09C 1/644* (2013.01); *C09C 2200/1054* (2013.01); *C09C 2210/40* (2013.01); *C09C 2220/20* (2013.01)

(58) Field of Classification Search
CPC ........................................................ A61K 8/26
See application file for complete search history.

(56) References Cited

FOREIGN PATENT DOCUMENTS

| DE | 102007062942 A1 * | 6/2008 | ............... A61K 8/26 |
|---|---|---|---|
| EP | 2965744 A1 * | 1/2016 | ........... A45D 29/001 |

* cited by examiner

*Primary Examiner* — Gina C Justice
(74) *Attorney, Agent, or Firm* — Fitch, Even, Tabin & Flannery LLP

(57) ABSTRACT

An embossed effect pigment includes a metallic substrate in platelet form with embossed structure having a periodic pattern with diffractive elements, said substrate having been produced by PVD methods, wherein the substrate has an elemental metal content of 80% to 100% by weight, based on the substrate, and wherein the effect pigment has been treated with a leafing additive for surface modification. A method of manufacture of an embossed effect pigment includes suspending a metallic substrate in in at least one solvent, adding a leafing additive to the suspension including the metallic substrate in the at least one solvent and stirring the suspension including the leafing additive, and separating the embossed effect pigment from the at least one solvent.

15 Claims, No Drawings

EMBOSSED EFFECT PIGMENT AND METHOD OF MANUFACTURE OF EMBOSSED EFFECT PIGMENT

The present invention relates to a surface-modified effect pigment and to a process for production thereof and to nail varnish compositions comprising said surface-modified effect pigment.

WO 2005/055965 A1 discloses cosmetic compositions such as nail varnishes containing embossed aluminum pigments with a rainbow effect. However, there is no disclosure of binders based on hydrocarbon resins.

EP 1 462 085 A1 discloses a nail varnish composition with a mirror effect which comprises particles having metallic luster in a proportion of ≥2% by weight, based on the total weight of the nail varnish composition, and texturing agents. EP 1 462 085 A1 does not disclose any surface-modified effect pigments. Moreover, this property right does not disclose diffractive effect pigments.

EP 1 299 066 A2 describes a nail varnish comprising aluminum platelets and having a mirror-like appearance. According to EP 1 299 066 A2, the nail varnish has to comprise nitrocellulose having a molecular weight of >56000 g/mol as film former for a mirror-like effect on a fingernail to be achievable. This property right does not disclose diffractive effect pigments.

EP 1 796 794 A1 discloses a cosmetic composition comprising a PVD aluminum pigment at a pigmentation level of 0.05% to 5.0% by weight, based on the total weight of the cosmetic composition, and at least one leafing additive. Leafing additives used are long-chain phosphoric esters or a mixture of multiple long-chain phosphoric esters. However, the leafing effect is not fully manifested in most nail varnishes. Moreover, this property right does not disclose diffractive effect pigments.

EP 2 248 514 A2 describes nitrocellulose-free nail varnish compositions comprising at least one styrene/maleic anhydride copolymer as high-gloss film former, at least one epoxy resin as co-film former, at least one reactive component and at least one solvent. The nitrocellulose-free nail varnish composition is said to have comparable or better adhesion properties than nitrocellulose-containing nail varnish compositions. The only colorants disclosed in EP 2 248 514 A2 are pearlescent pigments as effect pigments.

U.S. Pat. No. 6,692,830 B2 discloses fundamentally diffractive metal effect pigments with a rainbow effect that may also be coated with various interference layers. The pigments have various line densities.

EP 1901870 B1 describes the production of diffractive metal effect pigments having a median size d exceeding 75 μm.

EP 2598578 B1 discloses dark-colored embossed metal effect pigments.

Embossed metal effect pigments are known as such and are also used in nail varnishes. However, there is still a need for an improvement in the rainbow effect in nail varnishes.

It has been found that the effect pigments surface-modified in accordance with the invention do not show good results in all nail varnish systems as disclosed, for example, in EP 1796794 B2. Frequently, the leafing effect is lost on application or thereafter, with the associated effect that the optical properties of the effect pigments are not fully manifested.

It is an object of the present invention to provide a nail varnish composition comprising embossed effect pigments that has an improved rainbow effect and improved chroma. Moreover, if at all possible, brilliance should also be improved.

A further object is that of providing a process for producing the nail varnish of the invention.

In addition, a process for coating keratinous substrates with a nail varnish is to be provided.

The object underlying the invention is achieved by the provision of a nail varnish composition comprising
a) an embossed effect pigment comprising a metallic substrate in platelet form with embossed structure having a periodic pattern with diffractive elements, said substrate having been produced by PVD methods, and optionally at least one coating applied to the substrate, wherein the substrate has an elemental metal content of 80% to 100% by weight, based on the substrate, and wherein the effect pigment has been treated with a leafing additive for surface modification,
b) at least one hydrocarbon resin as binder,
c) at least one solvent or solvent mixture and
d) optionally further auxiliaries.

Preferred embodiments of the nail varnish composition of the invention can be found in dependent claims 2 to 12 of WO 2019/077021.

The object underlying the invention is likewise achieved by a process for producing the nail varnish composition of the invention, comprising the steps of
i) surface-modifying the effect pigment by means of a leafing additive in a dispersion in a solvent,
ii) dissolving the hydrocarbon resin in a solvent or solvent mixture,
iii) mixing and homogenizing the dispersion according to i) with the binder solution according to ii), and
iv) optionally supplementing with further solvent or solvent mixture.

A preferred embodiment of this process can be found in dependent claim 14 of WO 2019/077021.

In addition, the object is achieved by the provision of a process for coating a natural or synthetic fingernail, comprising the steps of:
a) coating the natural or synthetic fingernail with a nail varnish composition as claimed in any of claims 1 to 13 of WO 2019/077021 and then drying the nail varnish,
b) optionally subsequently coating the nail varnish with a clearcoat.

A preferred embodiment of this process can be found in dependent claim 16 of WO 2019/077021.

Nail Varnish Composition of the Invention:

The invention is directed to a nail varnish composition that enables and maintains the leafing effect of the effect pigments in an excellent manner.

This nail varnish composition of the invention comprises:
a) an effect pigment comprising a metallic substrate in platelet form with embossed structure having a periodic pattern with diffractive elements, said substrate having been produced by PVD methods, and optionally at least one coating applied to the substrate, wherein the substrate has an elemental metal content of 80% to 100% by weight, based on the substrate, and wherein the effect pigment has been treated with a leafing additive for surface modification,
b) at least one hydrocarbon resin as binder,
c) at least one solvent or solvent mixture and
d) optionally further auxiliaries.

The nail varnish composition of the invention comprising at least one surface-modified effect pigment, by contrast with most commercially available nail varnish compositions, preferably does not include any nitrocellulose or any cellulose acetate butyrate. The visual appearance of the nail varnish composition of the invention, after application and drying, is determined to a crucial degree by the at least one surface-modified embossed effect pigment.

The nail varnish composition of the invention comprises the at least one surface-modified embossed effect pigment preferably in a proportion from a range from 0.2% by weight to 7.0% by weight, further preferably from a range from 0.3% by weight to 5.0% by weight, more preferably from a range from 0.35% by weight to 3.0% by weight and most preferably from a range from 0.4% by weight to 2.0% by weight, based in each case on the total weight of the nail varnish composition.

In the nail varnish compositions of the invention, the embossed surface-modified effect pigments preferably arrange at the surface of applied nail varnish. According to the invention, "arrange at the surface" means that the surface-modified effect pigments, on the nail varnish base and/or proceeding from the nail varnish composition/air or nail varnish composition/overcoat interface, are in the third of the nail varnish composition that adjoins this interface in the direction of the varnished substrate. Preferably, the surface-modified effect pigments float in the nail varnish and become aligned at the nail varnish surface. The surface-modified effect pigments therefore show marked leafing characteristics in the nail varnish composition of the invention.

Due to these marked leafing characteristics of the surface-modified effect pigments, it is possible in accordance with the invention to produce nail varnish compositions that owe their visual appearance mainly to the at least one surface-modified effect pigment added to the nail varnish base. Therefore, the rainbow effect and also the chroma of the embossed effect pigments are manifested much better.

In further embodiments, it is also possible for further surface-modified, preferably non-diffractive effect pigments to be added to the nail varnish composition according to the optical effect to be achieved, in which case both the surface modification and the effect pigments may be different from one another. It is likewise possible to add conventional organic and/or inorganic pigments to the nail varnish composition of the invention.

Embossed Effect Pigments:

According to the invention, the nail varnish composition of the invention contains an effect pigment comprising a metallic substrate in platelet form with embossed structure having a periodic pattern with diffractive elements, said substrate having been produced by PVD methods and having a line density of 5000 to 20 000 lines/cm, and optionally at least one coating applied to the substrate, wherein the substrate has an elemental metal content of 80% to 100% by weight, based on the substrate.

According to the invention, the embossed structure has a periodic pattern with diffractive elements. The periodic pattern relates here to the smallest unit of the diffractive elements. The periodic diffractive structure preferably has 5000 to 20000 diffractive elements/cm, more preferably 9000-18000 diffractive elements/cm and most preferably 12000-16000 diffractive elements/cm. Within this range, predominantly visible light (wavelength about 400 to 800 nm) is diffracted at the diffractive elements by the known principle of a diffraction grid, as a result of which the viewer perceives a rainbow effect. However, it is also possible to diffract fractions of IR radiation and/or of UV radiation.

The periodicity essentially determines the diffracted wavelengths of the incident light. Specifically, this can be calculated by known formulae, as can be inferred, for example, from U.S. Pat. No. 6,692,830 B2.

Useful diffractive elements include, for example, symmetric triangles, asymmetric triangles, grooves in a wide variety of different forms, rectangular functions, circles, wavy lines, cones, trunctated cones, pimples, prisms, pyramids, truncated pyramids, cylinders, hemispheres, etc., and combinations of these geometric forms and bodies.

Geometric bodies having one or more surfaces arranged parallel to the pigment surface, for example trunctated cones, truncated pyramids, cylinders or rectangular functions, have a higher reflection capacity owing to these surfaces.

Geometric bodies that have oblique lateral faces based on the pigment surface enhance the rainbow effect. Oblique lateral faces are understood to mean lateral faces having an angle, based on the substrate, of 5° to 89°, preferably of 15° to 84°, even further preferably of 27° to 80°, even further preferably of 43° to 74°. Suitable geometric bodies are, for example, cones, trunctated cones, pyramids, truncated pyramids, etc.

In the case of trunctated cones, for example, there is both reflection at the top surface parallel to the pigment surface and an enhancement of the rainbow effect at the lateral surface. Correspondingly, in the case of truncated pyramids, there is reflection at the top surface and enhancement of the rainbow effect on the oblique lateral surfaces.

It will be appreciated that it is also possible in the case of trunctated cones or truncated pyramids to arrange the top face in a non-parallel manner to the pigment surface, but rather oblique to the pigment surface.

By means of the geometric bodies arranged on the surface of the metallic substrate in platelet form by embossing and/or forming, the rainbow effect and/or the reflection capacity of the effect pigment can be enhanced or the relative ratio of rainbow effect to reflection can be altered.

For instance, the geometric bodies may be separated into sections or else mixed with one another. It is of course also possible to arrange the geometric forms and geometric bodies in a superposed manner, such that, for example, geometric bodies are additionally arranged on a wavy structure.

In a further variant of the invention, it is possible for unembossed or unshaped, and therefore smooth, sections to be present alongside embossed and/or shaped sections on the metallic substrate surface in platelet form. In this way too, it is possible to alter the relative ratio of rainbow effect to reflection.

Preferably, the entire surface of the metallic substrate in platelet form has been provided with the diffractive structure, preferably embossed. However, it is also possible for just a portion of the metal effect pigment surface to have been provided with the diffractive structure, preferably embossed, or to have been shaped to a diffractive structure. Preferably at least 60%, more preferably at least 75% and most preferably at least 90% of the metal effect pigment surface has been embossed with a diffractive structure or formed to a diffractive structure.

In a particularly preferred embodiment, the diffractive structure comprises or consists of wavy, for example sinusoidal, lines, cones or trunctated cones. In a very particularly preferred embodiment, the diffractive structure comprises or consists of sinusoidal lines, since this shape is firstly particularly easy to emboss and secondly results in a very significant diffraction effect. In the case of these sinusoidal lines, the diffractive structure is preferably embossed on the entirety of the metallic substrate in platelet form.

In a preferred embodiment, the nail varnish composition of the invention contains an effect pigment comprising a metallic substrate in platelet form with embossed structure, wherein the metal is taken from the group consisting of aluminum, copper, chromium, iron or alloys thereof.

More preferably, the metallic substrate in platelet form with embossed structure contains or consists of a metal composed of aluminum, which gives particularly good reflectivity and is easily produced by PVD methods.

In order to be able to achieve a clearly perceptible effect, the diffractive structure, preferably line structure, preferably has a certain minimum depth since the physical effect of diffraction can otherwise be manifested only inadequately. Therefore, the diffractive structure should preferably have a depth (measured as "peak to valley" according to WO 2005/055965 A1) of at least 40 nm, preferably 40 nm to 600 nm and more preferably of 50 nm to 400 nm and most preferably of 100 nm to 250 nm.

Above 600 nm, the structure can no longer have overall stability. Below 40 nm, the diffractive effect is insufficiently pronounced.

The metallic embossed substrates in platelet form are produced by PVD methods.

Preferably, the metallic, engraved substrate in platelet form has an average thickness $h_{50}$ (median) from a range from 20 nm to 80 nm, more preferably from a range from 30 to 60 nm.

The median $h_{50}$ is preferably determined by the SEM method described in WO 2004/087816 A2 (pages 24 and 25).

Below 20 nm, the substrate is possibly too dark and can lose the necessary mechanical strength needed to obtain the embossed structure.

Above 80 nm, the metallic substrate becomes too thick to cause the necessary brilliance and hiding power.

The depth of the diffractive structure can therefore exceed the average layer thickness $h_{50}$ of the metallic substrate in platelet form.

The median size $d_{50}$ of the effect pigments with embossed structure is within a range of 5-120 μm, preferably within a range of 10-75 μm and most preferably within a range of 15-40 μm.

The $d_{50}$ is determined here by means of laser diffraction methods as the volume-averaged cumulative undersize curve of the size distribution (Fraunhofer diffraction) in the manner customary for the person skilled in the art. This is done using the Horiba LA-950 instrument from Horiba as measuring instrument.

The $h_{50}$ of the cumulative frequency distribution of the size distribution function indicates that 50% of the effect pigments analyzed have a size equal to or smaller than the particular value reported.

Below 5 μm, the number of the diffractive structures per pigment particle is too small to cause an effective rainbow effect. Above 120 μm, the effect pigment is too large to be orientated in a sufficiently plane-parallel manner to the finger substrate in the nail varnish formulation after the application to a synthetic or natural finger. In the case of poor orientation, the rainbow effect and the chroma are likewise distorted owing to a partly quenching superposition of the diffracted light emitted by differently oriented effect pigment particles.

If metal effect pigments are used in cosmetic formulations, they have to meet certain purity demands, for example the EU Cosmetic Regulation 1223/2009 or FDA 21CFR part 73.

If, for example, aluminum platelets are used as metallic substrate in platelet form, these preferably have an aluminum content of ≥97% by weight, further preferably of ≥98% by weight, more preferably of ≥99% by weight and most preferably of ≥99.7% by weight, based in each case on the total weight of the aluminum platelet. In a preferred embodiment, the aluminum platelets also have a mercury content of preferably ≤1 ppm, an arsenic content of preferably ≤2 ppm, a lead content of preferably ≤10 ppm, a cadmium content of preferably ≤1 ppm, a barium content of preferably ≤10 ppm, a chromium content of preferably ≤20 ppm, a nickel content of preferably ≤20 ppm, a copper content of preferably ≤20 ppm, a cobalt content of preferably ≤20 ppm, an antimony content of preferably ≤2 ppm, a selenium content of preferably ≤10 ppm and a zinc content of preferably ≤20 ppm.

In particular, it is preferable that the aluminum platelets have a mercury content of preferably ≤1 ppm, an arsenic content of preferably ≤2 ppm, a lead content of preferably ≤10 ppm, and a cadmium content of preferably ≤1 ppm.

If copper platelets are used as metallic substrate in platelet form, these preferably have a copper content of 95% by weight, further preferably of ≥96% by weight, more preferably of ≥97% by weight and most preferably of ≥98% by weight, based in each case on the total weight of the copper platelet. In a preferred embodiment, the copper platelets also have a mercury content preferably of ≤1 ppm, an arsenic content preferably of ≤3 ppm, a lead content preferably of ≤20 ppm, a cadmium content preferably of ≤15 ppm, a barium content preferably of ≤10 ppm, a chromium content preferably of ≤20 ppm, a nickel content preferably of ≤20 ppm, a cobalt content preferably of ≤20 ppm, an antimony content preferably of ≤2 ppm and a selenium content preferably of ≤10 ppm.

If gold bronze platelets are used as metallic substrate in platelet form, these preferably have a copper content from a range from 70% by weight to 95% by weight, a zinc content from a range from <5% by weight to <30% by weight, an aluminum content from a range from 0.01% by weight to ≤1.5% by weight, a tin content from a range from 0.001% by weight to ≤0.5% by weight, based in each case on the total weight of the gold bronze platelets. In a preferred embodiment, the gold bronze platelets also have a mercury content preferably of ≤1 ppm, an arsenic content preferably of ≤3 ppm, a lead content preferably of ≤20 ppm, a cadmium content preferably of ≤15 ppm, a barium content preferably of ≤10 ppm, a chromium content preferably of ≤20 ppm, a nickel content preferably of ≤20 ppm, a cobalt content preferably of ≤20 ppm, an antimony content preferably of ≤2 ppm and a selenium content preferably of ≤10 ppm.

In one embodiment, the nail varnish composition of the invention contains, as effect pigment, a metallic engraved substrate in metallic platelet form with diffractive elements that does not have any further optically active coatings.

This substrate is preferably composed of aluminum.

In a further-preferred embodiment, the metallic embossed substrates in platelet form to be used in accordance with the invention, apart from the coating needed in accordance with the invention, do not have further coating with a leafing additive. In this case, metal oxide layers that naturally form under air, for example an aluminum oxide layer, are not considered as coating.

In this case, the effect pigment consists solely of a metallic layer into which the embossed structure, preferably a line structure, has been embossed. Such effect pigments are particularly preferred since their total thickness is minimal owing to lack of further coatings. Such pigments can be incorporated particularly efficiently into nail varnishes.

The production of such effect pigments is described, for example, in EP 643745 B1 or EP 1901870 B1.

Such pigments are commercially available, for example under the Metalure® Prismatic and Silverdream Prismatic trade names from Eckart America.

In a further embodiment of the invention, the metallic, engraved substrate in platelet form, preferably an aluminum substrate, has optically active coatings containing at least one layer package composed of:
A) a low-refractive layer having a refractive index of <1.8 and
B) a high-refractive layer having a refractive index exceeding 2.0.

These layers are preferably also produced by means of PVD methods.

The low-refractive layer preferably consists of $SiO_2$, $Al_2O_3$, $B_2O_3$ or $MgF_2$.

The high-refractive coating present in this embodiment may comprise at least one high-refractive layer composed of or comprising at least one metal oxide, metal hydroxide and/or metal oxide hydrate, where the metal ion is preferably selected from the group of metals consisting of Ti, Fe, Sn, Mn, Zr, Sr, Ba, Ni, Ag, Zn, Cu, Cr and Co, and further preferably selected from the group of metals consisting of Ti, Fe, Sn, Zr, Zn and Cr, and especially preferably selected from the group of metals consisting of Ti and Fe.

In further embodiments, it is also possible to use high-refractive metal sulfides, for example $MoS_2$.

In a further embodiment, the high-refractive coating optionally present, alternatively or additionally to the layer comprising at least one metal oxide, metal hydroxide and/or metal oxide hydrate, may comprise at least one semitransparent metal layer. The metals of the semitransparent metal layer may be selected from the group consisting of Ag, Al, Cr, Ni, Au, Pt, Pd, Cu, Zn and Ti, preferably selected from the group consisting of Ag, Au and Cu. The semitransparent metal layer may of course also comprise alloys or mixtures of the above-listed metals. The average thickness of the semitransparent metal layer is preferably within a range from 1 nm to 30 nm, more preferably within a range from 4 nm to 26 nm and more preferably within a range from 7 nm to 21 nm.

In further embodiments, the metallic, engraved substrate in platelet form, preferably an aluminum substrate, has only a layer applied to both sides by PVD methods, preferably of low refractive index. Such layers are not intended to contribute to the optical activity of the effect pigment, but merely to impart mechanical stability thereto. Such effect pigments are described, for example, in WO 2000/34395.

For example, embossed effect pigments with corresponding coatings are supplied by Viavi (Santa Rosa, California, USA) under the SpectraFlair® trade name.

Further examples of such effect pigments have the following layer structures:
Al/$SiO_2$/Al/$SiO_2$/Al
Cr/$MgF_2$/Al/$MgF_2$/Cr
$MoS_2$/$SiO_2$/Al/$SiO_2$/$MoS_2$
$Fe_2O_3$/$SiO_2$/Al/$SiO_2$/$Fe_2O_3$ The production of such effect pigments is described, for example, in U.S. Pat. No. 6,749,777 B2.

In these effect pigments, the color impression is influenced not only by the diffraction by the diffractive structure but additionally by interference phenomena of the additional coatings. This can result in "disturbance" of the pure rainbow effect. In the context of this invention, the effect obtained is nevertheless also described as "rainbow effect".

In a further embodiment, the metallic, embossed substrate in platelet form consists of a mixed layer of metal, preferably predominantly in the form of nanometal, and a metal oxide, where the metal and metal oxide have the same metal. Such PVD effect pigments are described in EP 2598578 B1 and are notable in that the reflection of these pigments is very low. These are virtually black effect pigments, but these nevertheless have a rainbow effect owing to their embossment. Metals envisaged here are preferably aluminum or chromium. The average thicknesses of such embossed effect pigments are within a range from 40 to 130 nm.

In a further embodiment, the surface-modified effect pigments of the invention, based on metallic substrates in platelet form with coatings, that are to be used in a nail varnish composition preferably have an average total thickness $h_{50}$ from a range from 20 nm to 4000 nm, further preferably from a range from 30 nm to 3000 nm, more preferably from a range from 70 nm to 2000 nm and most preferably from a range from 230 nm to 1300 nm. Average total thickness is understood to mean the complete average thickness of the surface-modified effect pigment, i.e. metallic substrate in platelet form plus optional coating plus surface modification.

Leafing Additive:

An essential constituent of the present invention is the provision of a nail varnish in which the leafing properties of the surface-modified effect pigments are very well manifested.

A preferred leafing additive for surface modification of the metallic substrate in platelet form is at least one compound taken from the group consisting of phosphoric ester-containing, phosphonic acid-containing, fatty acid-containing and/or silane-containing compounds or mixtures thereof.

In a preferred embodiment, the leafing additives usable for surface modification used are those from the group consisting of phosphoric esters of the general formula:

$$(R—O)_x—P(O)(OR^1)_{(3-x)} \quad (I)$$

and/or of phosphonic esters and/or phosphonic acids of the general formula

$$R—P(O)(OR^2)(OR^3) \quad (II).$$

In this case, x=1 to 3 and the R, $R^1$, $R^2$ and $R^3$ radicals are defined as follows:
R=linear and/or branched alkyl radical having a carbon chain from a range from $C_8$ to $C_{20}$ and
$R^1$=H, linear and/or branched alkyl radical having a carbon chain from a range from $C_1$ to $C_6$, preferably $C_1$ to $C_3$, where $R^1$ when x=1 may be identical or different, and
$R^2$=$R^3$=H, linear and/or branched alkyl radical having a carbon chain from a range from $C_1$ to $C_6$, preferably $C_1$ to $C_3$, where $R^2$ and $R^3$ may be identical or different.

In the phosphoric esters of formula (I), x in preferred embodiments is 1 or 2, where mixtures between the mono- and diphosphoric ester are also possible. R is further preferably $C_{10}$ to $C_{20}$ and especially preferably $C_{12}$ to $C_{18}$ and very especially preferably $C_{12}$ to $C_{16}$. In further-preferred embodiments, R=$C_{12}$ to $C_{18}$ and $R^1$=H.

In further-preferred embodiments, the additive used for surface modification of the embossed effect pigment is phosphonic acid, phosphonic esters and phosphoric esters from the group of laurylphosphonic acid methyl ester, laurylphosphonic acid ethyl ester, laurylphosphonic acid (R=12) or monocetylphosphoric ester, dicetylphosphoric ester (R=16) and mixtures thereof.

As leafing additive is most preferably monocetylphosphoric ester. Dicetylphosphoric ester (R=16) and mixtures thereof used.

The fatty acids usable for surface modification may be fatty acids of the general formula $$R'\text{---COOH} \quad (III)$$

where the R' radical is a linear or branched alkyl radical having a carbon chain from a range from $C_{12}$ to $C_{26}$, preferably from a range from $C_{14}$ to $C_{24}$, further preferably from a range from $C_{16}$ to $C_{22}$ and especially preferably from a range from $C_{18}$ to $C_{20}$.

In a preferred embodiment, surface modification of the effect pigments usable in a nail varnish composition of the invention is accomplished using fatty acids with R' a linear unsubstituted alkyl moiety having a carbon chain from a range from $C_{12}$ to $C_{20}$, preferably from a range from $C_{14}$ to $C_{18}$.

Since the effect pigments are produced by PVD methods, by contrast with metal effect pigments obtained by grinding, they do not contain any fatty acids. Therefore, the fatty acids must also be applied to the embossed effect pigments as surface modification.

The silanes usable for surface modification may be silanes of the general formula $$R''\text{---Si(OR}^4)_3 \quad (IV)$$

where the R" and $R^4$ radicals are preferably defined as follows:
R"=linear and/or branched alkyl radical having a carbon chain from a range from $C_8$ to $C_{24}$, preferably from a range from $C_{10}$ to $C_{22}$, especially preferably from a range from $C_{12}$ to $C_{18}$, and $R^4$=linear and/or branched alkyl radical having a carbon chain from a range from $C_1$ to $C_4$, preferably from a range from $C_1$ to $C_3$ and especially preferably from a range from $C_1$ to $C_2$. In further embodiments, the alkyl radical R" may comprise in at least one substituent selected from the group consisting of —OH, —OCH$_3$, —OC$_2$H$_5$, —NH$_2$, linear and/or branched alkyl radical having a carbon chain from a range from $C_1$ to $C_6$.

It is especially preferred that the embossed effect pigments are coated with the additive in a separate step before they are introduced into the nail varnish system.

A process of the invention for surface modification of the embossed effect pigments comprises the following steps:
i. suspending the embossed effect pigment comprising a metallic substrate in platelet form with embossed structure in at least one solvent,
ii. adding the leafing additive at optionally elevated temperature to the suspension from step i. and stirring the suspension then obtained,
iii. separating and optionally drying the surface-modified effect pigment obtained in step ii. from the solvent.

Solvents used here are solvents that firstly have maximum compatibility with the nail varnish system of the invention and are physiologically compatible, and secondly are capable of sufficiently dissolving the leafing additive.

When phosphoric esters, phosphonic esters, phosphonic acids or fatty acids are used as leafing additives, preferred solvents are ethyl acetate and butyl acetate and mixtures thereof, and very particular preference is given to butyl acetate.

The optionally elevated temperature serves for better solubility of the additive in the solvent and is preferably within a range from 40 to 100° C. or up to the boiling point of the solvent, and more preferably within a range from 50 to 90° C.

If the leafing additive used is an organofunctional silane, this is preferably applied to the surface of the embossed effect pigments by a sol-gel reaction. The solvents used here are preferably ethanol, isopropanol or mixtures thereof. It is optionally possible to add suitable amounts of water and of acidic and/or basic catalyst to the solvent. The water results in better hydrolysis of the alkoxy groups of the silane.

The leafing additive for surface modification is preferably used in an amount from a range from 5% by weight to 50% by weight, more preferably from a range from 10% by weight to 40% by weight and most preferably from a range from 15% by weight to 35% by weight, based in each case on the total weight of the embossed effect pigment used.

Since the amounts of the additive specified here are based on the starting material, the actual amount of additive in the ready-coated embossed effect pigment may be smaller since, for example, in the case of an amount of 50% by weight, not all the additive can be absorbed onto the pigment surface. Accordingly, smaller amounts of the leafing additives may be found in the nail varnish of the invention comprising the embossed effect pigments.

However, the effect of the quite high amounts of additive in the starting material is very high and dense coating of the effect pigment surface with the additive.

In a further particularly preferred embodiment of the invention, in the coating process, the leafing additive used for surface modification of embossed effect pigments is at least one phosphonic ester and/or phosphonic acid of the formula (II) in a total amount from a range from 10% by weight to 50% by weight, more preferably from a range from 15% by weight to 45% by weight, and most preferably from a range from 20% by weight to 40% by weight, based in each case on the total weight of the embossed effect pigment.

Below the specified amounts of phosphonic ester and/or phosphonic acid, insufficient leafing of the effect pigments takes place. Above the specified amounts of phosphonic ester and/or phosphonic acid, excessively large amounts of the phosphonic ester and/or phosphonic acid may possibly be introduced into the finished nail varnish composition. It is particularly preferable here that the effect pigments are coated with the phosphonic ester and/or phosphonic acid in a separate step before they are introduced into the nail varnish system.

In particular preferred embodiments, the leafing additive used in the process according to the invention is at least one phosphoric ester of the formula (I) where each R is a linear alkyl radical with preferably $C_{10}$ to $C_{20}$, more preferably $C_{12}$ to $C_{18}$, and $R^1$=H, in a total amount from a range from 15% by weight to 40% by weight, further preferably a range from 20% by weight to 35% by weight, based on the total weight of the embossed effect pigment used.

In a further preferred embodiment, the leafing additive used for surface modification of the embossed effect pigments based on metallic embossed substrates in platelet form is at least one fatty acid in a total amount from a range from preferably 5% by weight to 40% by weight, more preferably from a range from 10% by weight to 38% by weight and most preferably from a range from 20% by weight to 35% by weight, based in each case on the total weight of the effect pigment used.

In a further preferred embodiment, the leafing additive used for surface modification of the embossed effect pigments based on metallic embossed substrates in platelet form is at least one silane in a total amount preferably from a range from 5% by weight to 39% by weight, further preferably from a range from 10% by weight to 35% by weight, more preferably from a range from 15% by weight to 32% by weight and most preferably from a range from 18% by weight to 30% by weight, based in each case on the total weight of the embossed effect pigment used.

Below the amounts of the specific substances to be used as starting material for surface modification that are specified for the surface-modified embossed effect pigments of the invention or for the various effect pigment/additive combinations described above for the respectively for different effect pigment types, insufficient leafing of the effect pigments takes place. Above the amounts of the additives specified in each case, it is possible for excessively large amounts of the additives to be introduced into the finished nail varnish composition and to cause troublesome effects therein.

A portion of the leafing additives used will not adhere to the surface of the embossed effect pigment at the above-described higher reference values of the ranges of the starting concentrations, since the surface thereof is already saturated. For high and uniform coverage, however, it is necessary to provide sufficient amounts of additive that may also include a distinct excess, since only in that case is an intense leafing effect to be expected.

Naturally, the amount of the leafing additive can be reduced with the specific surface area of the embossed effect pigment, and vice versa. A smaller specific surface area exists in the case of very large and/or thick embossed effect pigments. Thick embossed effect pigments are obtained especially in the case of those where the metallic embossed substrate has been coated with further layers.

According to the invention, "total amount" is understood to mean the complete amount of starting leafing additive material, irrespective of whether the starting material is exclusively at least one phosphoric ester or exclusively at least one phosphonic acid or phosphonic ester or a mixture of at least one phosphoric ester and at least one phosphonic acid or a mixture of different phosphonic acids or a mixture of different fatty acids or a mixture of different silanes.

The embossed effect pigments that have been surface-modified with the leafing additive in accordance with the invention may, as well as the nail varnish of the invention, also find use in other cosmetic formulations. The surface-modified effect pigments are notable for their excellent leafing characteristics in nail varnish compositions and especially in the nail varnish composition of the invention.

Binder:

The nail varnish compositions of the invention comprise at least one hydrocarbon resin as binder, where the binder preferably has a binder solids content from a range from 25% by weight to 64% by weight, further preferably from a range from 25% by weight to 60% by weight, further preferably from a range from 28% by weight to 55% by weight, more preferably from a range from 29% by weight to 50% by weight and most preferably from a range from 35% by weight to 43% by weight, based in each case on the total weight of the nail varnish composition.

Below a binder content of 25% by weight, no good optical effects resulting from the effect pigments were any longer apparent in the nail varnish applied.

Above 63% by weight, the optical quality of the effect pigments likewise declines and the viscosity of the nail varnish compositions of the invention increasingly becomes too high.

Hydrocarbon resins are understood to mean synthetic resins that form through reaction of hydrocarbons (excluding olefins) with themselves in the presence of aluminum chloride or sulfuric acid as catalyst (see https://www.s-pektrum.de/lexikon/chemie/kohlenwasserstoffharze/4959). In accordance with their structure, the hydrocarbon resins are divided into the three groups of petroleum resins, coal tar resins and terpene resins. Coumarone-indene resins are the most important group of the coal tar resins. Also counted among the hydrocarbon resins are the reaction products of xylene and formaldehyde, the xylene-formaldehyde resins. In preferred embodiments, nail varnish compositions comprising aromatic hydrocarbon resins are used.

Further particularly preferred aromatic hydrocarbon resins are resins that are obtained predominantly to entirely by polymerization of different purified styrene monomers. Preferably, the styrene monomers here are optically largely transparent ("water-clear").

The hydrocarbon resins are a particular group of resins that are used for paints and printing inks.

This specific resin class in no way comprises resins based merely on hydrocarbons in a quite general sense.

Hydrocarbon resins are produced in a known manner by heating high-boiling fractions from gasoline pyrolysis (pyrolysis oil) or the isoprene-free $C_5$ fraction from gasoline pyrolysis in the presence of aluminum chloride. The hydrocarbon resins are soluble in most organic solvents, for example esters, ethers, hydrochlorocarbons and aromatics.

Without being bound to a theory, the inventors suspect that, in the case of use of polar binders, the effect pigments coated with suitable additives are still partly wetted by the binder and therefore do not have the desired leafing effect. By contrast, the resins in the nail varnish composition of the invention are unusually nonpolar for nail varnish compositions and accordingly do not wet the effect pigments. As a result, the embossed effect pigments are likely to be able to better develop the leafing effect.

Usually, "hydrocarbon resins" are understood to mean polymers of very low molecular weight with molar masses below 2000 g/mol By contrast, it has been found that, surprisingly hydrocarbon resins with higher-molecular molar masses may also be used in accordance with the invention.

The nail varnish compositions of the invention preferably comprise, as binders, hydrocarbon resins having an average molecular weight ($M_W$) from a range from 800 to 6500 g/mol, preferably from a range from 900 to 6000 g/mol or from a range from 1200 to 5500 g/mol. The average molecular weight $M_W$ has been determined by means of gel permeation chromatography (GPC) with a polystyrene standard.

In a preferred embodiment, the nail varnish compositions of the invention comprise at least two different hydrocarbon resins having a first average molecular weight $M_W$ from a range from 1000 to 2000 g/mol and a second average molecular weight $M_W$ from a range from 4000 to 5900 g/mol in a weight ratio of 1:1 to 1:10, preferably 1:1 to 1:8, more preferably 1:1 to 1:4 and most preferably 1:1 to 1:2 of the two different hydrocarbon resins.

In a particularly preferred embodiment, the nail varnish compositions of the invention comprise at least two different hydrocarbon resins having a first average molecular weight $M_W$ from a range from 1200 to 1600 g/mol and a second average molecular weight $M_W$ from a range from 4500 to 5500 g/mol in a weight ratio of 1:1 to 1:10, preferably 1:1 to 1:8, more preferably 1:1 to 1:4 and most preferably 1:1 to 1:2 of the two different hydrocarbon resins.

Preferably, these mixtures relate to aromatic hydrocarbon resins that are obtained predominantly to entirely by polymerization of different purified styrene monomers.

The nail varnish compositions of the invention may comprise, as binder, hydrocarbon resins such as, for example, Kristalex F100 Hydrocarbon Resin, Kristalex 5140 Hydrocarbon Resin, Kristalex 3070 Hydrocarbon Resin, Kristalex 3085 Hydrocarbon Resin, Kristalex F115 Hydrocarbon Resin, each from Eastman. These are resins that are obtained predominantly to entirely by polymerization of different purified styrene monomers.

Preferably, the nail varnish compositions of the invention comprise, as binder, the hydrocarbon resins Kristalex F100 Hydrocarbon Resin and Kristalex 5140 Hydrocarbon Resin.

In particularly preferred embodiments, the nail varnish composition of the invention contains hydrocarbon-containing resin in an amount that makes up 80% to 100% by weight, further preferably 90% to 99% by weight and especially preferably 95% to 100% by weight of the overall organic binder.

The use of hydrocarbon resins in nail varnishes as a main constituent of the binder is unusual to the inventors' knowledge. Hydrocarbon resins are usually very rare constituents of nail varnishes and, if they are used, they are used in comparatively small proportions together with other binders.

In further embodiments, therefore, the nail varnish composition of the invention contains virtually no additional binders, if any, from the group of nitrocellulose, polyester resins, polyvinyl resins, alkyd resin, epoxy resins or cellulose acetate butyrate. These binders are preferably present in proportions of below 10% by weight, further preferably below 5% by weight and more preferably of below 1% by weight and most preferably below 0.1% by weight, based in each case on the total weight of the hydrocarbon resins and additional binders. These binders have been found to be a hindrance if anything to the achievement of a truly strong rainbow effect.

Without being bound to a theory, the inventors suspect that, in nail varnish compositions containing the abovementioned binders, these at least partly wet the effect pigments owing to their stronger polarity, and hence these have poorer leafing properties.

Solvent:

The nail varnish compositions of the invention preferably contain particular solvents. Solvents that may be added to the nail varnish compositions of the invention are, for example, ethyl acetate, butyl acetate or isopropanol.

Preferably, the nail varnish composition of the invention contains a mixture of isopropanol, ethyl acetate and butyl acetate as solvent.

More preferably, the nail varnish composition of the invention contains the solvent mixture of isopropanol, ethyl acetate and butyl acetate in an amount of 70% to 100% by weight, further preferably 75% to 98% by weight, based on the total solvent in the nail varnish composition.

It is unimportant here whether these preferred solvents are introduced by the binders or the effect pigment dispersion.

In further preferred embodiments, in this solvent mixture, the proportion of butyl acetate is 30% to 60% by weight and more preferably 35% to 55% by weight, based on the overall solvent.

In a further particularly preferred embodiment, the proportion of isopropanol is below 20% by weight, preferably below 15% by weight, and further preferably below 10% by weight, based in each case on the total solvent.

Excessively high proportions of isopropanol in the nail varnish composition of the invention lead to a poor visual appearance of the effect pigments. This is probably attributable to excessively rapid drying of the nail varnishes after application thereof.

The nail varnish compositions of the invention are applicable in an extremely simple manner to a human or synthetic fingernail and/or toenail. During application, they are notable for good levelling and, after subsequent drying, form a homogeneous film on a human or synthetic fingernail and/or toenail.

In preferred embodiments, the nail varnish of the invention contains 50% by weight to 70% by weight, preferably 55% by weight to 68% by weight and more preferably 57% to 65% by weight of solvent, based in each case on the weight of the overall nail varnish.

Below a solvent content of 55% by weight, there is an excessively significant rise in the viscosity of the nail varnish and the effect pigments are unable to adopt an optimal orientation, which leads to a reduction in up to loss of the rainbow effect.

Above a solvent content of 70% by weight, there is too great a reduction in the viscosity of the nail varnish, which leads to poorly controllable application of the nail varnish to the fingernail.

Further Constituents:

The nail varnish compositions of the invention may additionally contain one or more further constituents. Particularly mentioned are here plasticizers and antioxidants.

Plasticizers used may, for example, be glycols and derivatives thereof, for example diethylene glycol ethyl ether, diethylene glycol methyl ether, diethylene glycol butyl ether or additionally diethylene glycol hexyl ether, ethylene glycol ethyl ether, ethylene glycol methyl ether, ethylene glycol butyl ether, ethylene glycol hexyl ether, glycol esters, derivatives of propylene glycol and especially propylene glycol phenyl ether, propylene glycol diacetates, dipropylene glycol butyl ether, tripropylene glycol butyl ether, propylene glycol methyl ether, dipropylene glycol ethyl ether, tripropylene glycol methyl ether and diethylene glycol methyl ether, propylene glycol butyl ether, or mixtures thereof.

In addition may as plasticizers used especially esters of carboxylic acids, for example of citrates, especially trimethyl citrate, tributyl citrate, trimethylacetyl citrate, tributylacetyl citrate, tri-2-ethylhexyl acetyl citrates or of phthalates, especially dimethoxyethyl phthalate; or of phosphates, especially tricresyl phosphate, tributyl phosphate, triphenyl phosphate, tributoxyethyl phosphates or of tartrates, especially dibutoxy tartrate; adipates, carbonates, sebacates; benzyl benzoate, butyl acetyl ricinoleate, glyceryl acetyl ricinoleate, butyl glycolate, camphor, glycerol triacetates, N-ethyl-o,p-toluenesulfonamide, oxyethylene compounds, for example oxyethylene oils, especially vegetable oils, for example castor oil, hydrocarbon oils and mixtures thereof.

Preferred plasticizers are especially hydrocarbon oils.

The proportions by weight of the plasticizers in the overall nail varnish composition are preferably a range from 0% to 15% by weight, further preferably from 1% to 10% by weight, and more preferably from 5% to 10% by weight.

The nail varnish composition of the invention may additionally contain one or more antioxidants.

"Antioxidants" are understood to mean compounds that protect the constituents of the nail varnish of the invention, especially the hydrocarbon binders, from the effect of oxygen, heat, ozone and/or UV radiation. It is possible to use one or more compounds of this kind. Examples of compounds of this kind are IRGANOX® 1010, IRGANOX® 565, IRGANOX® 1076 (from BASF) or sulfur-containing antioxidants, for example zinc dibutyldithiocarbamate (PERKACIT ZDBC (from Performance additives Italy S.p.A)).

The antioxidants are preferably used in amounts from a range from 0% to 5% by weight, further preferably from a range from 0.05% to 1% by weight, based on the overall nail varnish composition.

Further Additives:

The nail varnish composition of the invention may additionally contain customary further additives as known to those skilled in the art.

Further additives of this kind are, for example, antisettling agents, preservatives, oils, waxes, free-moiety scavengers, wetting additives, dispersing aids, wetting aids, antifoams, perfume, neutralizing agents, thickeners, UV blockers, humectants, vitamins, proteins and mixtures thereof.

By contrast with the leafing additives, these further additives are not added to the nail varnish composition until during the formulation of this composition, and are not added separately to the embossed effect pigment beforehand.

In further embodiments, the nail varnish composition of the invention preferably does not contain any antisettling agents. Astonishingly, any surface-modified effect pigment that has settled out can generally be redispersed by simply shaking even without the addition of antisettling agents.

The nail varnish composition of the invention preferably has a viscosity of 10 sec to 16 sec, measured with a DIN flow cup (DIN 4 mm) according to DIN 53211.

In preferred embodiments, the nail varnish composition of the invention contains embossed aluminum PVD effect pigments having a periodic pattern with diffractive elements that are preferably lines having a line density of 11000 to 16000 lines/cm. These embossed aluminum PVD effect pigments are preferably coated with laurylphosphonic acid methyl ester, laurylphosphonic acid ethyl ester, laurylphosphonic acid (R=12) or monocetylphosphoric ester, dicetylphosphoric ester (R=16) and mixtures thereof as leafing additive. Binders used are aromatic hydrocarbon resins based on styrene monomers, and the solvent used is a mixture of isopropanol, ethyl acetate and butyl acetate, where this solvent mixture accounts for 70% to 100% by weight of the total solvent of the nail varnish composition.

In a further preferred embodiment, the nail varnish composition of the invention contains aluminum PVD effect pigments having an average thickness $h_{50}$ from a range from 14 to 40 nm, preferably from a range from 15 to 35 nm, and also at least two different aromatic hydrocarbon resins and a mixture of isopropanol, ethyl acetate and butyl acetate as solvent, where this solvent mixture accounts for 70% to 100% by weight of the total solvent in the nail varnish composition. Here too, leafing additives used are preferably phosphoric acid cetyl ester or laurylphosphonic acid.

Process:

The invention further provides a process for producing the nail varnish composition of the invention, comprising the steps of
  i) surface-modifying the embossed effect pigment by means of an additive in a dispersion in a solvent,
  ii) dissolving the hydrocarbon resin in a solvent or solvent mixture,
  iii) mixing and homogenizing the dispersion according to i) with the binder solution according to ii).

The dissolving of the hydrocarbon resin in a solvent in step ii) is preferably effected in one solvent or a mixture of at least two, preferably three, solvents. More preferably, the solvent mixture used is a mixture of isopropanol, ethyl acetate and butyl acetate.

Butyl acetate is preferably used as the sole solvent.

In further preferred embodiments, the solvent in step i) will likewise consist of isopropanol, ethyl acetate and butyl acetate or a mixture of these, in order not to introduce further, possibly disruptive solvents into the nail varnish.

Preference is given here to executing step i) in accordance with the following process already discussed further up.

A process of the invention for surface modification of the embossed effect pigments comprises the following steps:
  i. suspending the embossed effect pigment comprising a metallic substrate in platelet form with embossed structure in at least one solvent,
  ii. adding the leafing additive at optionally elevated temperature to the suspension from step i. and stirring the suspension then obtained,
  iii. separating and optionally drying the surface-modified embossed effect pigment obtained in step ii. from the solvent.

It is further preferable, in the selection of the metallic embossed effect pigments, to choose those that are present in their original dispersion in a solvent from the preferred group of isopropanol, ethyl acetate and butyl acetate or mixtures thereof, since the solvent of the metal effect pigment dispersion likewise gets into the nail varnish of the invention in small amounts unless complex rewetting steps are used.

Especially when single-layer embossed metal effect pigments are used, especially single-layer embossed aluminum effect pigments, these effect pigments produced by PVD methods are always in a dispersion since they have a tendency to agglomerate as a powder.

The invention likewise provides a method of coating a natural or synthetic fingernail, comprising the steps of:
  a) coating the natural or synthetic fingernail with a nail varnish composition of the invention and then drying the nail varnish,
  b) optionally subsequently coating the nail varnish with a clearcoat.

The application of the clearcoat considerably increases the abrasion resistance of the nail varnish. Owing to the marked leafing effect of the effect pigments in the nail varnish, it naturally has comparatively low abrasion resistance.

Step a) may likewise be preceded by coating of the natural or synthetic fingernail with a clearcoat in order to establish a very even surface. This course of action is advisable if the fingernails have high roughness.

The subsequent coating with clearcoat in step b) can be conducted with the same clearcoat as or a different clearcoat than the nail varnish of the invention. However, this clearcoat in no case contains effect pigments since these would cover over the desired effect of the nail varnish of the invention.

However, the clearcoat in step b) may contain conventional color pigments or dyes. Specifically in combination with metallic PVD aluminum pigments or with thin aluminum effect pigments produced by wet grinding and having an $h_{50}$ of 20 to below 100 nm, it is possible to achieve very visually appealing effects. In this case, the nail varnish compositions of the invention that have been pigmented with the effect pigments preferably have specular gloss after step a).

In a further embodiment, the nail varnish composition of the invention may be overcoated with a low-viscosity UVcuring clearcoat in order to increase the abrasion resistance of the nail varnish composition of the invention.

It is also possible with preference to use solvent-based clearcoats. Without being bound to a theory, the clearcoat is preferably based on polar binders that interact only to a minor degree with the hydrocarbon resins of the clearcoat of the invention. In particularly preferred embodiments, these clearcoats are based on binders such as polyvinyl butyral (PVB), polyvinylpyrrolidone (PVP) or mixtures thereof.

In addition, the clearcoat preferably contains solvents that do not (partly) dissolve the nonpolar hydrocarbon resins of the varnish of the invention. For example, it is possible with preference to use isopropanol for this purpose. Otherwise, the leafing effect pigments can also be partly dissolved again and their orientation can be disrupted, which disrupts the specular gloss effect.

Surprisingly, these preferred clearcoats have very good bond strength on the nail varnish of the invention.

Embossed Surface-Modified Effect Pigments of the Invention:

It is a further object of the present invention to provide an embossed effect pigment for use in a nail varnish composition that has an improved rainbow effect, and also improved chroma and improved brilliance.

The invention likewise relates to an embossed effect pigment comprising a metallic substrate in platelet form with embossed structure, which is produced by PVD methods and by means of coating with a leafing additive composed of phosphoric esters of the general formula:

$$(R-O)_x-P(O)(OR^1)_{(3-x)} \qquad (I)$$

where x=1 or 2, R=linear and/or branched alkyl radical having a carbon chain from a range from $C_{12}$ to $C_{20}$, and $R^1$=H Preferably, this embossed effect pigment is a single-layer effect pigment with a metallic substrate composed of aluminum. Further preferably, the embossed structures are lines having a line density of 5000 to 20 000 lines/cm. The lines are preferably wavy lines ("sinusoidal"), since this structure is particularly easy to produce.

According to the invention, this preferred embossed effect pigment is treated with a leafing additive for surface modification, consisting of monocetylphosphoric ester, dicetylphosphoric ester (R=16) and mixtures thereof.

In a further-preferred embodiment, the embossed surface-modified effect pigment is produced in a process comprising the following steps:
 i. suspending the embossed effect pigment comprising a metallic substrate in platelet form with embossed structure in at least one solvent,
 ii. adding the leafing additive at optionally elevated temperature to the suspension from step i. and stirring the suspension then obtained,
 iii. separating and optionally drying the surface-modified embossed effect pigment obtained in step ii. from the solvent.

The leafing additive, based on the total amount of substrate, is used here within a range from 15% by weight to 50% by weight.

An excess of additive is needed to bring about a stable leafing effect.

In a further aspect of the invention, the above-described embossed surface-modified effect pigments may also be used in other nail varnishes.

In a further aspect of the invention, the above-described embossed surface-modified effect pigments may be used in further cosmetic applications. Examples of these include body powders, face powders, pressed or loose powders, powder creams, eye makeup, for example eyeshadow, mascara, eyeliner, liquid eyeliner, eyebrow pencil, lip balm, lipstick, lip gloss, lip liner, hairstyling compositions such as hairspray, hair mousse, hair gel, hair wax, hair mascara, permanent or semipermanent hair dyes, temporary hair dyes or skincare compositions such as lotions, gels, emulsions.

The surface-modified effect pigments of the invention are combined here with raw materials, auxiliaries and active ingredients suitable for the respective application. The total concentration of surface-modified effect pigments of the invention in the cosmetic formulation may be between 0.001% by weight for rinse-off products and 40.0% by weight for leave-on products, based in each case on the total weight of the formulation.

Aspects:

A first aspect 1) of the present invention relates to a nail varnish composition comprising a) an embossed effect pigment comprising a metallic substrate in platelet form with embossed structure having a periodic pattern with diffractive elements, said substrate having been produced by PVD methods, and optionally at least one coating applied to the substrate, wherein the substrate has an elemental metal content of 80% to 100% by weight, based on the substrate, and wherein the effect pigment has been treated with a leafing additive for surface modification, b) at least one hydrocarbon resin as binder, c) at least one solvent or solvent mixture and
d) optionally further auxiliaries.

In one aspect 2), the present invention relates to nail varnish compositions according to aspect 1, wherein the leafing additive is taken from the group consisting of phosphoric esters of the general formula:

$$(R-O)_x-P(O)(OR^1)_{(3-x)} \qquad (I)$$

and/or from phosphonic esters and/or phosphonic acids of the general formula $$R-P(O)(OR^2)(OR^3) \qquad (II)$$

or from fatty acids of the general formula $$R'-COOH \qquad (III)$$

or from organofunctional silanes of the general formula $$R''-Si(OR^4)_3 \qquad (IV)$$

where x=1 to 3 and the R, R', R", $R^1$, $R^2$, $R^3$ and $R^4$ radicals are defined as follows:
 R=linear or branched alkyl radical having a carbon chain from a range from $C_8$ to $C_{20}$;
 R'=linear or branched alkyl radical having a carbon chain from a range from $C_{12}$ to $C_{26}$;
 R"=linear or branched alkyl radical having a carbon chain from a range from $C_8$ to $C_{24}$;
 $R^1$=H, linear and/or branched alkyl radical having a carbon chain from a range from $C_1$ to $C_6$, preferably $C_1$ to $C_3$, where $R^1$ when x=1 may be identical or different;
 $R^2$=$R^3$=H, linear and/or branched alkyl radical having a carbon chain from a range from $C_1$ to $C_6$, preferably $C_1$ to $C_3$, where $R^2$ and $R^3$ may be identical or different, and
 $R^4$=linear and/or branched alkyl radical having a carbon chain from a range from $C_1$ to $C_4$.

In one aspect 3), the present invention relates to nail varnish compositions according to aspect 2, wherein the additive is a phosphoric ester of formula (I) with R=$C_{12}$ to $C_{18}$ and $R^1$=H.

In one aspect 4), the present invention relates to nail varnish compositions according to either of aspects 2 and 3, wherein the additive used for surface modification of the substrate or coating is laurylphosphonic acid methyl ester, laurylphosphonic acid ethyl ester, laurylphosphonic acid (R=12) and mixtures thereof, or monocetylphosphoric ester, dicetylphosphoric ester (R=16) and mixtures thereof.

In one aspect 5), the present invention relates to nail varnish compositions according to any of the preceding aspects, wherein the metallic substrate in platelet form with embossed structure is a metal taken from the group consisting of aluminum, copper, chromium, iron and alloys thereof.

In one aspect 6), the present invention relates to nail varnish compositions according to aspect 5, wherein the metallic substrate in platelet form with embossed structure is aluminum.

In one aspect 7), the present invention relates to nail varnish compositions according to any of the preceding aspects, wherein the metallic substrate in platelet form with embossed structure has 5000 to 20 000 diffractive elements/cm.

In one aspect 8), the present invention relates to nail varnish compositions according to aspect 6), wherein the metallic, engraved substrate in platelet form composed of aluminum does not have any optically active coatings.

In one aspect 9), the present invention relates to nail varnish compositions according to aspects 1 to 6, wherein the metallic, engraved substrate in platelet form composed of aluminum has optically active coatings containing at least one layer package composed of:
  A) a low-refractive layer having a refractive index of <1.8 and
  B) a high-refractive layer having a refractive index exceeding 2.0.

In one aspect 10), the present invention relates to a nail varnish composition according to any of the preceding aspects, wherein the metallic, engraved substrate in platelet form has an average thickness $h_{50}$ from a range from 20 nm to 80 nm.

In one aspect 11), the present invention relates to nail varnish compositions according to any of the preceding aspects, wherein the metallic, engraved substrate in platelet form has a median size $d_{50}$ from a range of 5-120 μm.

In one aspect 12), the present invention relates to nail varnish compositions according to aspect 11), wherein the embossed effect pigment has a median size $d_{50}$ from a range of 15-40 μm.

In one aspect 13), the present invention relates to nail varnish compositions according to aspects 1 to 4, wherein the metallic, engraved substrate in platelet form consists of a mixed layer of metal predominantly in the form of nanometal and a metal oxide, wherein the metal and the metal oxide have the same metal and are taken from the group consisting of aluminum and chromium.

In one aspect 14), the present invention relates to nail varnish compositions according to any of the preceding aspects, wherein the hydrocarbon resin is taken from the group consisting of coumarone-indene resins, polystyrene-containing resins, resins derived from formaldehyde resins by polycondensation, and mixtures thereof.

In one aspect 15), the present invention relates to nail varnish compositions according to aspect 14, wherein the hydrocarbon resin is a polystyrene-containing resin which is obtained predominantly to entirely by polymerization of different styrene monomers, especially largely optically transparent styrene monomers.

In one aspect 16), the present invention relates to nail varnish compositions according to any of the preceding aspects, wherein the hydrocarbon resin accounts for 80% to 100% by weight of the overall organic binder.

In one aspect 17), the present invention relates to nail varnish compositions according to any of the preceding aspects, wherein the hydrocarbon resin consists of at least two different hydrocarbon resins having a first average molecular weight $M_W$ from a range from 1000 to 2000 g/mol and a second average molecular weight $M_W$ from a range from 4000 to 5900 g/mol in a weight ratio of 1:1 to 1:10.

In one aspect 18), the present invention relates to nail varnish compositions according to aspect 17, wherein the hydrocarbon resin consists of at least two different hydrocarbon resins having an average molecular weight $M_W$ from a range from 1200 to 1600 g/mol and an average molecular weight $M_W$ from a range from 4500 to 5500 g/mol in a weight ratio of 1:1 to 1:10.

In one aspect 19), the present invention relates to nail varnish compositions according to any of the preceding aspects, wherein the content of hydrocarbon resins is within a range from 25% by weight to 63% by weight, based on the overall nail varnish composition.

In one aspect 20), the present invention relates to nail varnish compositions according to any of the preceding aspects, comprising, as solvent, a mixture of isopropanol, ethyl acetate and butyl acetate, wherein the solvent mixture of isopropanol, ethyl acetate and butyl acetate accounts for 70% to 100% by weight of the overall solvent.

In one aspect 21), the present invention relates to nail varnish compositions according to aspect 20, wherein the proportion of isopropanol is below 20% by weight, preferably below 15% by weight, based on the overall solvent.

In one aspect 22), the present invention relates to nail varnish compositions according to any of the preceding aspects, comprising, as further auxiliaries, plasticizers, antioxidants, antisettling agents, preservatives, oils, waxes, free radical scavengers, wetting additives, dispersing aids, wetting aids, antifoams, perfume, neutralizing agents, thickeners, UV blockers, humectants, vitamins, proteins and mixtures thereof.

In one aspect 23), the present invention relates to a process for producing the nail varnish compositions according to aspects 1 to 22, comprising the steps of
  i) surface-modifying the embossed effect pigment by means of a leafing additive in a dispersion in a solvent,
  ii) dissolving the hydrocarbon resin in a solvent or solvent mixture,
  iii) mixing and homogenizing the dispersion according to i) with the binder solution according to ii), and
  iv) optionally supplementing with further solvent or solvent mixture.

In one aspect 24), the present invention relates to a process according to aspect 23, wherein step i) is effected by a process comprising the following steps:
  i. suspending the embossed effect pigment comprising a metallic substrate in platelet form with embossed structure in at least one solvent,
  ii. adding the leafing additive at optionally elevated temperature to the suspension from step i. and stirring the suspension then obtained,
  iii. separating and optionally drying the surface-modified embossed effect pigment obtained in step ii. from the solvent.

In one aspect 25), the present invention relates to a process for coating a natural or synthetic fingernail, comprising the steps of:

a) coating the natural or synthetic fingernail with a nail varnish composition according to any of aspects 1 to 22 and then drying the nail varnish,
b) optionally subsequently coating the nail varnish with a clearcoat.

In one aspect 26), the present invention relates to a process according to aspect 25, characterized in that the nail varnish is coated with a solvent-based clearcoat based on binders from the group consisting of polyvinyl butyral, polyvinylpyrrolidone and mixtures thereof.

In one aspect 27), the present invention relates to an embossed effect pigment comprising a metallic substrate in platelet form with embossed structure, which is produced by PVD methods and by means of coating with a leafing additive composed of phosphoric esters of the general formula:

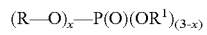

where x=1 or 2, R=linear and/or branched alkyl radical having a carbon chain from a range from $C_{12}$ to $C_{20}$, and $R^1$=H.

In one aspect 28), the present invention relates to an embossed effect pigment according to aspect 27, wherein the metallic substrate consists of aluminum and the embossed structure are lines having a line density of 5000 to 20 000 lines/cm.

In one aspect 29), the present invention relates to an embossed effect pigment according to either of aspects 27 and 28, wherein the leafing additive used for surface modification of the metallic embossed substrate is monocetylphosphoric ester, dicetylphosphoric ester (R=16) and mixtures thereof.

In one aspect 30), the present invention relates to an embossed effect pigment according to any of aspects 27 to 29, wherein the leafing additives are applied by a process comprising the following steps:
  i. suspending the embossed effect pigment comprising a metallic substrate in platelet form with embossed structure in at least one solvent,
  ii. adding the leafing additive at optionally elevated temperature to the suspension from step i. and stirring the suspension then obtained,
  iii. separating and optionally drying the surface-modified embossed effect pigment obtained in step ii. from the solvent,
and wherein the leafing additive, based on the total amount of substrate, is used within a range from 15% by weight to 50% by weight.

In a further aspect 31), the present invention relates to the use of the surface-modified, embossed effect pigments according to aspects 27 to 30 in further cosmetic applications taken from the group consisting of body powders, face powders, pressed or loose powders, powder creams, eye makeup, for example eyeshadow, mascara, eyeliner, liquid eyeliner, eyebrow pencil, lip balm, lipstick, lip gloss, lip liner, hairstyling compositions such as hairspray, hair mousse, hair gel, hair wax, hair mascara, permanent or semipermanent hair dyes, temporary hair dyes or skincare compositions such as lotions, gels, emulsions.

EXAMPLES

The examples which follow serve for further description of the invention and are not supposed to be restrictive in any way. All percentages are percentages by weight. The terms NVC (nonvolatile content), proportion of solids and solids content are usable interchangeably.

I Production of the Surface-Modified Effect Pigments of the Invention

Example 1

In a 1 L jacketed reactor, 198 g of the PVD aluminum effect pigment dispersion of commercially available Metalure Prismatic H-50550 AE (dispersion in ethyl acetate, solids content 5.05% by weight, $D_{50}$ (Horiba LA-950)=about 50 μm, from ECKART America) was dispersed in a solvent according to table 1 below at 200 rpm/min and heated to 80° C. Subsequently, the phosphoric acid cetyl ester additive (CAS number: 3539-43-3, Hostaphat CC 100, from Clariant) according to table 1 below, dissolved in 20 g of the solvent (AE) used for dispersion, was added to the aluminum effect pigment dispersion. After stirring at 80° C. for 6 hours, the mixture was cooled down and filtered through a Buechner funnel. Surface-modified PVD aluminum effect pigments were obtained as 5-25% dispersions. These have been supplemented with ethyl acetate to give a pigment dispersion having an NVC of 5%.

Examples 2 to 10

The procedure was as in example 1, except that the PVD aluminum effect pigment used in some cases was commercially available Silverdream Prismatic H-50720 (dispersion in ethyl acetate, solids content 7.05% by weight, $D_{50}$ (Horiba LA-950)=about 20 μm, from ECKART America) and the additive used was in some cases laurylphosphonic acid (abbreviation: LPS), and the solvent used was butyl acetate (BA) rather than ethyl acetate (AE). The details relating to the substances used, the amounts thereof and the absorption temperature can be found in table 1 below.

The solvents used in the final supplementation of the product separated by suction filtration to give the pigment dispersion and the nonvolatile contents (NVCs) of the dispersions established can respectively be found in columns 4 and 3 of table 2 and table 3.

Comparative example 1: Here, the uncoated commercially available PVD aluminum effect pigment dispersion Metallic Prismatic H-50550 AE with engraved wavy line lattice (line density: 12500 lines/cm) was used.

Comparative example 2: Here, the uncoated commercially available PVD aluminum effect pigment dispersion Silverdream Prismatic H-50720 with engraved wavy line lattice (line density: 12500 lines/cm) was used.

TABLE 1

Experimental parameters for coating of the engraved PVD aluminum pigments with additive

| Example | Engraved PVD pigment used | Amount of PVD pigment dispersion/ amount of Al | Amount of solvent for dispersion of the PVD pigment [g] | Additive | Amount of additive [in % by wt., based on aluminum] | Solvent for dissolving additive | Coating temperature [° C.] |
|---|---|---|---|---|---|---|---|
| 1 | Metalure Prismatic H-50550 AE | 198 g/10 g | 269.3 | Hostaphat CC 100 | 20% | AE* | 60 |

TABLE 1-continued

Experimental parameters for coating of the engraved PVD aluminum pigments with additive

| Example | Engraved PVD pigment used | Amount of PVD pigment dispersion/ amount of Al | Amount of solvent for dispersion of the PVD pigment [g] | Additive | Amount of additive [in % by wt., based on aluminum] | Solvent for dissolving additive | Coating temperature [° C.] |
|---|---|---|---|---|---|---|---|
| 2 | Metalure Prismatic H-50550 AE | 198 g/10 g | 269.3 | Hostaphat CC 100 | 30% | AE | 60 |
| 3 | Silverdream Prismatic H-50720 | 141.8/10 g | 325.5 | Hostaphat CC 100 | 20% | BA | 80 |
| 4 | Silverdream Prismatic H-50720 | 141.8/10 g | 325.5 | Hostaphat CC 100 | 30% | BA** | 80 |
| 5 | Silverdream Prismatic H-50720 | 141.8/10 g | 325.5 | LPS | 20% | BA | 80 |
| 6 | Silverdream Prismatic H-50720 | 141.8/10 g | 325.5 | LPS | 30% | BA | 80 |
| 7 | Metalure Prismatic H-50550 AE | 198 g/10g | 269.3 | Hostaphat CC 100 | 20% | BA | 80 |
| 8 | Metalure Prismatic H-50550 AE | 198 g/10g | 269.3 | Hostaphat CC 100 | 30% | BA | 80 |
| 9 | Metalure Prismatic H-50550 AE | 198 g/10g | 269.3 | LPS | 20% | BA | 80 |
| 10 | Metalure Prismatic H-50550 AE | 198 g/10g | 269.3 | LPS | 30% | BA | 80 |

*AE: ethyl acetate;
**BA: butyl acetate 85/15: mixture of 85% butyl acetate and 15% n-butanol II Production of the Nail Varnish Compositions of the Invention IIa Production of the Nail Varnish Clearcoat of the Invention:

In a suitable stirred vessel, a 70% by weight binder solution BM1 was produced. For this purpose, 70 g of the binder Kristalex F100 Hydrocarbon Resin ($M_w$=about 1300 g/mol, from Eastman) was added to an initial charge of 30 g of butyl acetate 85/15 while stirring and cooling (12° C.) with the Dispermat CNf2 dissolver (from Getzmann GmbH), and then the mixture was stirred at 3000 to 4000 rpm/min for a further 30 minutes.

In a second suitable stirred vessel, a 60% by weight binder solution BM2 was produced. For this purpose, 60 g of the binder Kristalex 5140 Hydrocarbon Resin ($M_w$=about 4900 g/mol, from Eastman) was added to an initial charge of 40 g of butyl acetate 85/15 while stirring and cooling (12° C.) with the Dispermat CNf2 dissolver (from Getzmann GmbH), and then the mixture was stirred at 3000 to 4000 rpm/min for a further 30 minutes.

The nonvolatile content (binder solids content) of the above-described binder solutions was determined according to DIN EN ISO 3251:2008.

Comparative nail clearcoat: The unpigmented Nail Polish Base 18840 nail clearcoat from International Lacquers was used as a comparative lacquer. This nail lacquer contains nitrocellulose as binder, and the solvents ethyl acetate, n-butyl acetate and propan-2-ol.

IIb Production of the Pigmented Nail Varnish Compositions of the Invention

For production of the nail varnish compositions of the invention according to example 11, the entirety of an initial charge of 5.49 g of BM1 and 12.84 g of BM2 was well dispersed by stirring. Then 2.08 g of the surface-modified PVD pigment from example 1 and subsequently 2.04 g of isopropyl alcohol, 3.27 g of N-butyl acetate 85/15 and 0.87 g of ethyl acetate were added, and the nail varnish was well dispersed.

The nail varnish compositions according to examples 11 to 20 were produced analogously to example 11, choosing the amounts of the individual components so as to achieve the quantity ratios listed in table 2 below, each in wt.-% by weight, based on the overall nail varnish composition.

As comparative examples 3 to 12, defined amounts of the respective surface-modified embossed PVD aluminum effect pigment (according to examples 1 to 10) and non-surface-modified embossed PVD aluminum effect pigments (comparative examples 1 and 2) according to table 3 below were likewise initially provided and incorporated into the comparative nail varnish.

As further comparative examples, the effect pigments that have not been surface-modified with additives from comparative examples 1 and 2 were each incorporated with the nail varnish of the invention (comparative examples 14 and 15) and with the comparative nail clearcoat (comparative examples 16 and 17).

The exact quantities (in % by weight) can be found in tables 2 and 3 below. (There is no comparative example 13.)

TABLE 2

Quantity ratios in % by weight of the added components of the nail varnishes of the invention

| Sample | PVD pigment used according to | NVC of PVD pigment dispersion % | SV*** | Weight of PVD pigment dispersion % | Addition of AE* % | Addition of BA** 85/15% | Addition of iso-propanol % | BM1% | BM2% | Σ % |
|---|---|---|---|---|---|---|---|---|---|---|
| Comparative example 14 | Comparative example 1 | 5 | AE | 11.52 | | 12.88 | 3.39 | 21.64 | 50.59 | 100.0 |
| Comparative example 15 | Comparative example 2 | 7 | AE | 8.23 | 3.31 | 12.88 | 3.39 | 21.64 | 50.59 | 100.0 |
| Example 11 | Example 1 | 7.13 | AE | 8.08 | 3.43 | 12.88 | 3.39 | 21.64 | 50.59 | 100.0 |
| Example 12 | Example 2 | 7.94 | AE | 7.25 | 4.25 | 12.88 | 3.39 | 21.64 | 50.59 | 100.0 |
| Example 13 | Example 3 | 6.41 | BA 85/15 | 8.98 | 10.99 | 4.49 | 3.39 | 21.64 | 50.59 | 100.0 |
| Example 14 | Example 4 | 7 | BA 85/15 | 8.23 | 10.99 | 5.20 | 3.39 | 21.64 | 50.59 | 100.0 |
| Example 15 | Example 5 | 7.35 | BA 85/15 | 7.84 | 10.99 | 5.67 | 3.39 | 21.64 | 50.59 | 100.0 |
| Example 16 | Example 6 | 7.31 | BA 85/15 | 7.88 | 10.99 | 5.55 | 3.39 | 21.64 | 50.59 | 100.0 |
| Example 17 | Example 7 | 6.68 | BA 85/15 | 8.62 | 10.99 | 4.84 | 3.39 | 21.64 | 50.59 | 100.0 |
| Example 18 | Example 8 | 4.27 | BA 85/15 | 13.49 | 10.99 | 0 | 3.39 | 21.64 | 50.59 | 100.0 |
| Example 19 | Example 9 | 6.64 | BA 85/15 | 8.67 | 10.99 | 4.84 | 3.39 | 21.64 | 50.59 | 100.0 |
| Example 20 | Example 10 | 6.25 | BA 85/15 | 9.21 | 10.99 | 4.25 | 3.39 | 21.64 | 50.59 | 100.0 |

*AE: ethyl acetate;
**BA: butyl acetate;
***SV: solvent of the pigment dispersion of the coated PVD pigment

TABLE 3

Quantity ratios in % by weight of the added components for the comparative examples of the nail varnishes

| Sample | PVD pigment used according to | NVC % | SV | Weight of PVD pigment dispersion % | Addition of AE % | Addition of BA 85/15% | Addition of isoprop. % | Base 18840% | Σ % |
|---|---|---|---|---|---|---|---|---|---|
| Comparative example 16 | Comparative example 1 | 5 | AE | 9.75 | 1.67 | — | — | 88.58 | 100.0 |
| Comparative example 17 | Comparative example 2 | 7 | AE | 6.96 | 4.46 | — | — | 88.58 | 100.0 |
| Comparative example 3 | Example 1 | 7.13 | AE | 6.84 | 4.58 | — | — | 88.58 | 100.0 |
| Comparative example 4 | Example 2 | 7.94 | AE | 6.14 | 5.28 | — | — | 88.58 | 100.0 |
| Comparative example 5 | Example 3 | 6.41 | BA 85/15 | 7.61 | — | 3.81 | — | 88.58 | 100.0 |
| Comparative example 6 | Example 4 | 7 | BA 85/15 | 6.96 | — | 4.46 | — | 88.58 | 100.0 |
| Comparative example 7 | Example 5 | 7.35 | BA 85/15 | 6.63 | — | 4.79 | — | 88.58 | 100.0 |
| Comparative example 8 | Example 6 | 7.31 | BA 85/15 | 6.67 | — | 4.75 | — | 88.58 | 100.0 |
| Comparative example 9 | Example 7 | 6.68 | BA 85/15 | 7.30 | — | 4.12 | — | 88.58 | 100.00 |
| Comparative example 10 | Example 8 | 4.27 | BA 85/15 | 11.42 | — | 0.00 | — | 88.58 | 100.0 |
| Comparative example 11 | Example 9 | 6.64 | BA 85/15 | 7.34 | — | 4.08 | — | 88.58 | 100.0 |
| Comparative example 12 | Example 10 | 6.25 | BA 85/15 | 7.80 | — | 3.62 | — | 88.58 | 100.0 |

TABLE 4

Final quantity ratios of the individual components of the nail varnish compositions of the invention and of the comparative examples in % by weight, based on the overall nail varnish composition

| Sample | Al content % | BA % total | Kristalex F100% | Kristalex 5140% | Isopropanol % total | AE % total | Base 18840% total | Σ % |
|---|---|---|---|---|---|---|---|---|
| Comparative example 14 | 0.58 | 39.61 | 15.15 | 30.36 | 3.39 | 12.12 | — | 100.0 |
| Comparative example 15 | 0.58 | 39.61 | 15.15 | 30.36 | 3.39 | 12.15 | — | 100.0 |
| Example 11 | 0.58 | 39.61 | 15.15 | 30.36 | 3.39 | 12.12 | — | 100.0 |
| Example 12 | 0.58 | 39.61 | 15.15 | 30.36 | 3.39 | 12.13 | — | 100.0 |
| Example 13 | 0.58 | 39.52 | 15.15 | 30.36 | 3.39 | 10.99 | — | 100.0 |
| Example 14 | 0.58 | 39.57 | 15.15 | 30.36 | 3.39 | 10.99 | — | 100.0 |
| Example 15 | 0.58 | 39.57 | 15.15 | 30.36 | 3.39 | 10.99 | — | 100.0 |
| Example 16 | 0.58 | 39.57 | 15.15 | 30.36 | 3.39 | 10.99 | — | 100.0 |
| Example 17 | 0.58 | 39.57 | 15.15 | 30.36 | 3.39 | 10.99 | — | 100.0 |
| Example 18 | 0.58 | 39.57 | 15.15 | 30.36 | 3.39 | 10.99 | — | 100.0 |
| Example 19 | 0.58 | 39.57 | 15.15 | 30.36 | 3.39 | 10.99 | — | 100.0 |
| Example 20 | 0.58 | 39.57 | 15.15 | 30.36 | 3.39 | 10.99 | — | 100.0 |
| Comparative example 16 | 0.49 | 0.00** | — | — | —** | 10.93** | 88.58* | 100.0 |
| Comparative example 17 | 0.49 | 0.00 | — | — | — | 10.94 | 88.58 | 100.0 |
| Comparative example 3 | 0.49 | 0.00 | — | — | — | 10.93 | 88.58 | 100.0 |
| Comparative example 4 | 0.49 | 0.00 | — | — | — | 10.93 | 88.58 | 100.0 |
| Comparative example 5 | 0.49 | 10.93 | — | — | — | 0.00 | 88.58 | 100.0 |
| Comparative example 6 | 0.49 | 10.94 | — | — | — | 0.00 | 88.58 | 100.0 |
| Comparative example 7 | 0.49 | 10.94 | — | — | — | 0.00 | 88.58 | 100.0 |
| Comparative example 8 | 0.49 | 10.93 | — | — | — | 0.00 | 88.58 | 100.0 |
| Comparative example 9 | 0.49 | 10.93 | — | — | — | 0.00 | 88.58 | 100.0 |
| Comparative example 10 | 0.49 | 10.93 | — | — | — | 0.00 | 88.58 | 100.0 |
| Comparative example 11 | 0.49 | 10.93 | — | — | — | 0.00 | 88.58 | 100.0 |
| Comparative example 12 | 0.49 | 10.93 | — | — | — | 0.00 | 88.58 | 100.0 |

*The exact content of binder in the commercially available comparative nail varnish 18840 was not determined.

**The exact contents of the solvents in the commercially available comparative nail varnish 18840 were not analyzed. In this table, for comparative examples 3 to 12, only the added proportions by weight of ethyl acetate and butyl acetate were listed. Isopropanol was not added.

III Characterization of the Optical Properties of Nail Varnish Compositions

IIIa Determination of Chroma (25° Geometry)

To determine the visual appearance of the nail varnish compositions of the invention and of the nail varnish compositions from the comparative examples, the respective nail varnish composition was applied to contrast charts in a wet film thickness of 100 μm by means of a spiral applicator (K Control Coater model 623, from Erichsen) and then dried at room temperature. As an indirect measure of leafing characteristics, the chroma (25° geometry) of the nail varnish compositions thus applied was analyzed by the BYK Mac instrument (from BYK Gardner).

The values were determined at at least 5 different sites in the nail varnish application.

Table 5 below lists the averages formed therefrom for chroma (25° geometry).

Since this colorimetric parameter is supposed to rise with rising leafing effect of the pigments, it can be regarded as an indirect measure of the leafing characteristics of the embossed PVD pigments.

IIIb: Rainbow Effect and Brilliance:

The quality of the rainbow effect was assessed visually from a scale from 0 (no rainbow effect) to 10 (excellent rainbow effect) on the applicator drawdowns. Using the colorimeters available on the market, measurement of the optical effects of embossed effect pigments that are based on diffraction processes is barely viable, and therefore a visual assessment was preferred here.

Additionally likewise assessed by the same grade system was brilliance, for which values measured with conventional colorimeters can likewise be not very meaningful.

TABLE 5

Results for the visual appearance of all examples and comparative examples from applicator drawdowns

| Pigments used | Comparative examples (Nail Polish Base 181340) | | | Examples (Nail varnish of the invention) | | |
|---|---|---|---|---|---|---|
| | Rainbow effect visual | Brilliance visual | Chroma 25° colorimetry | Rainbow effect visual | Brilliance visual | Chroma 25° colorimetry |
| Comparative Example 1 | 1 | 2 | 11.7 | 0 | 0 | 1.1 |
| Example 1 | 1 | 2 | 12.2 | 3 | 2 | 11.8 |
| Example 2 | 1 | 2 | 13.2 | 3 | 2 | 15.8 |
| Example 3 | 1 | 2 | 9.8 | 3 | 3 | 17.7 |
| Example 4 | 1 | 2 | 10.5 | 2 | 2 | 11.6 |
| Example 5 | 1 | 2 | 9.1 | 2 | 2 | 10.1 |
| Example 6 | 1 | 2 | 9.4 | 3 | 3 | 16.7 |
| Comparative Example 2 | 2 | 1 | 9.3 | 0 | 0 | 1.1 |
| Example 7 | 2 | 1 | 8.4 | 8 | 8 | 44.7 |
| Example 8 | 2 | 1 | 9.0 | 10 | 10 | 55.9 |
| Example 9 | 2 | 1 | 9.5 | 6 | 6 | 32.8 |
| Example 10 | 2 | 1 | 8.9 | 6 | 6 | 31.2 |

IV Results:

All inventive examples 1 to 10 have a higher rainbow effect compared to the corresponding comparative examples in the commercially available nail varnish system. The differences are particularly major in the case of the embossed PVD pigment with a $d_{50}$ of about 20 μm (examples 7 to 10). In these examples, distinct differences are likewise apparent in the brilliance and in the chroma in the two paint systems. In the case of the coarser embossed PVD pigment, a trend to higher chroma values is likewise apparent, although no improvements were apparent in brilliance.

It was also found that, for the embossed PVD pigment having a $d_{50}$ of about 20 μm, examples coated with Hostaphat CC100 (cetylphosphoric ester) tended to give the best results compared to examples coated with laurylphosphonic acid (cf. examples 7 and 8 with examples 8 and 10). For the coarser embossed PVD pigments, however, this trend is not clear.

In all cases, the embossed PVD pigments used without additive pretreatment are poor with regard to rainbow effect and brilliance both in the comparative nail varnish system and in the inventive nail varnish system (comparative examples 1 and 2). It is apparent that the leafing effect of the embossed PVD pigments induced by the additive treatment is essential to the occurrence of an appealing rainbow effect.

The invention claimed is:

1. An embossed effect pigment comprising a metallic substrate in platelet form with embossed structure having a periodic pattern with diffractive elements, the substrate having been produced by PVD methods, wherein the substrate has an elemental metal content of 80% to 100% by weight, based on the substrate, and wherein the effect pigment has been treated with a leafing additive for surface modification, wherein the leafing additive has the formula:

$(R-O)_x-P(O)(OR^1)_{(3-x)}$ wherein x=1 or 2, R is a linear or branched alkyl radical having a carbon chain ranging from $C_8$ to $C_{20}$ and $R^1$ is H.

2. The embossed effect pigment according to claim 1, wherein the metallic substrate in platelet form includes aluminum with an embossed structure having 5,000 to 20,000 diffractive elements/cm.

3. The embossed effect pigment according to claim 1, wherein R is a linear or branched alkyl radical having a carbon chain ranging from $C_{12}$ to $C_{18}$.

4. The embossed effect pigment according to claim 1, wherein the leafing additive includes laurylphosphonic acid (R=12), monocetylphosphoric ester, dicetylphosphoric ester (R=16), or mixtures thereof.

5. The embossed effect pigment according to claim 1, wherein the substrate contains at least 80 wt-% aluminum.

6. The embossed effect pigment according to claim 1, wherein R is a linear or branched alkyl radical having a carbon chain ranging from $C_{12}$ to $C_{20}$.

7. The embossed effect pigment according to claim 1, wherein the metallic substrate is a single layered substrate made from aluminum.

8. An embossed effect pigment comprising a metallic substrate in platelet form with embossed structure having a periodic pattern with diffractive elements, the substrate having been produced by PVD methods, wherein the substrate has an elemental metal content of 80% to 100% by weight, based on the substrate, and wherein the effect pigment has been treated with a leafing additive for surface modification, wherein the leafing additive has the formula:

$(R-O)_x-P(O)(OR^1)_{(3-x)}$ wherein x=1 or 2, R is a linear or branched alkyl radical having a carbon chain ranging from $C_8$ to $C_{20}$ and $R^1$ is H, the embossed effect pigment having been produced by a process comprising:
suspending the metallic substrate in at least one solvent,
adding the leafing additive to the suspension comprising the metallic substrate and the at least one solvent and stirring the suspension including the leafing additive,
separating the embossed effect pigment from the at least one solvent, wherein the amount of the leafing additive on the embossed effect pigment is in a range of 15 to 50 wt. %, based on the metallic substrate.

9. The embossed effect pigment according to claim 8, wherein adding the leafing additive to the suspension of the metallic substrate in the at least one solvent is conducted at a temperature within a range from 40° C. to 100° C.

10. The embossed effect pigment according to claim 8, wherein the process further comprises drying the embossed effect pigment treated with the leafing additive that has been separated from the at least one solvent.

11. A method treating an embossed metallic substrate, the substrate being in platelet form with embossed structure having a periodic pattern with diffractive elements, the substrate having been produced by PVD methods, wherein the substrate has an elemental metal content of 80% to 100% by weight, based on the substrate, the method comprising:

suspending the embossed metallic substrate in at least one solvent to form a suspension;

adding a leafing additive to the suspension, wherein the leafing additive has the formula:

$(R{-}O)_x\text{-}P(O)(OR^1)_{(3-x)}$ wherein x=1 or 2, R is a linear or branched alkyl radical having a carbon chain ranging from $C_8$ to $C_{20}$ and $R^1$ is H;

stirring the suspension, whereby the embossed metallic substrate undergoes surface modification to result in an embossed effect pigment; and separating the embossed effect pigment from the at least one solvent;

wherein the amount of the leafing additive on the embossed effect pigment is in the range of 15 to 50 wt. %, based on the weight of the metallic substrate.

12. The method according to claim 11, wherein the at least one solvent comprises one or more of ethylacetate and butylacetate.

13. The method according to claim 11, wherein the at least one solvent is butylacetate.

14. The method according to claim 11, wherein adding the leafing additive to the suspension of the metallic substrate in the at least one solvent is conducted at a temperature within a range from 40° C. to 100° C.

15. The method according to claim 11, further comprising drying the embossed effect pigment treated with the leafing additive that has been separated from the at least one solvent.

* * * * *